United States Patent
Matsuda et al.

[11] Patent Number: 5,840,066
[45] Date of Patent: Nov. 24, 1998

[54] INFUSION CATHETER

[75] Inventors: Takehisa Matsuda, Minou; Nobumasa Tsutsui, Nagoya; Jun Inada, Kasugai, all of Japan

[73] Assignee: Tokai Kobunshi Kagaku Kabushikigaisha, Nagoya, Japan

[21] Appl. No.: 735,135

[22] Filed: Oct. 22, 1996

[30] Foreign Application Priority Data

Oct. 26, 1995 [JP] Japan .................................. 7-278992

[51] Int. Cl.⁶ .................................................. A61M 29/00
[52] U.S. Cl. ............................................. 604/96; 604/102
[58] Field of Search .............................. 604/96, 101–103; 606/194

[56] References Cited

U.S. PATENT DOCUMENTS

| | | | |
|---|---|---|---|
| 4,983,166 | 1/1991 | Yamawaki | 604/96 |
| 5,046,503 | 9/1991 | Schneiderman | 128/692 |
| 5,167,239 | 12/1992 | Cohen et al. | 128/772 |
| 5,284,473 | 2/1994 | Calabria | 604/53 |
| 5,295,961 | 3/1994 | Niedesbauser et al. | 604/96 |
| 5,334,154 | 8/1994 | Samson et al. | 604/102 |
| 5,344,402 | 9/1994 | Crocker . | |
| 5,383,853 | 1/1995 | Jung et al. | 604/96 |
| 5,423,745 | 6/1995 | Todd et al. | 604/53 |
| 5,569,184 | 10/1996 | Crocker et al. | 604/53 |

FOREIGN PATENT DOCUMENTS

| | | |
|---|---|---|
| 0 369 012 A1 | 5/1990 | European Pat. Off. . |
| 39 38 727 A1 | 10/1990 | Germany . |
| S2-13464 | 1/1990 | Japan . |
| S2-283380 | 11/1990 | Japan . |
| 4261668 | 9/1992 | Japan . |
| 4-64709 | 10/1992 | Japan . |
| 5184681 | 7/1993 | Japan . |
| 7132146A | 11/1993 | Japan . |
| 7136283A | 11/1993 | Japan . |
| 7204277A | 2/1994 | Japan . |
| 7328124A | 3/1994 | Japan . |

*Primary Examiner*—Wynn Wood Coggins
*Assistant Examiner*—Cris L. Rodriguez
*Attorney, Agent, or Firm*—Davis and Bujold

[57] ABSTRACT

An infusion catheter having a catheter shaft with a distal end, an inflatable and contractible balloon provided adjacent the distal end but spaced therefrom, a blood passage with two openings for passing blood through the balloon, and first and second lumens. The first lumen communicating with the balloon to inflate and contract the balloon, and the second lumen including a medicine discharge port located between the balloon and one opening of the blood passage to supply medicine to a lesion part of a blood vessel.

13 Claims, 6 Drawing Sheets

FIG. 6C

INFUSION CATHETER

FIELD OF THE INVENTION

This invention relates to infusion catheters in general, and more particularly to infusion catheters for use in the local administration of medicine to a blood vessel.

BACKGROUND OF THE INVENTION

Infusion catheters for administering medicine to a local place in a blood vessel are known and described, for example, in Japanese patent laid-open Nos. 4-261668 and 5-184681.

With the infusion catheter, a concentrated medicine can be administered locally in the blood vessel. Therefore, a small amount of medicine can be effectively used, and the harmful side effect from the medicine can be minimized. During the administration of the medicine, the infusion catheter can maintain the blood flow via a bypass connecting the upstream side and the downstream side of the place under treatment. Therefore, rather long-term treatment can be practiced.

However, conventional infusion catheters are not without shortcomings.

Consider, for example, percutaneous transluminal coronary angioplasty or PTCA, where the place to be treated is expanded with a balloon catheter and medicine is administered to the expanded place to prevent the recurrence of stenosis. With the infusion catheter proposed in the laid-open patent application No. 4-261668, the expansion of the place to be treated can precede the administration of the medicine.

This prior-art infusion catheter is composed of two balloons. While the stenosed part is expanded with one of the balloons, however, the other balloon inadvertently exerts pressure on a part of the blood vessel away from the stenosed part of the blood vessel. This undesirable pressure may damage the blood vessel, thereby creating an additional stenosed portion.

Alternatively, the infusion catheter proposed in the laid-open patent application No. 5-184681 is used for administering medicine to the already expanded part. The configuration of the infusion catheter is not suitable for the expansion step. Specifically, the infusion catheter has a cavity or a pocket for accommodating medicine in the outer periphery of a balloon. The stenosed part is insufficiently expanded by the balloon having this medicine accommodating pocket. Therefore, the stenosed part needs to be expanded with another balloon catheter. After the balloon catheter is evulsed, the proposed infusion catheter must be inserted for the administration of the medicine. This two catheter process is not only cumbersome, but requires additional time to administer.

SUMMARY OF THE INVENTION

Wherefore, an object of the present invention is to provide an infusion catheter for expanding only the lesion part of a blood vessel and applying a concentrated medicine to the expanded lesion part.

To attain this or other object, a first aspect of the present invention provides an infusion catheter including an inflatable and contractible balloon, a medicine discharge port located adjacent the distal end of the balloon for discharging the medicine to the blood vessel, and a blood passage provided with a first opening at the proximal side before the balloon and a second opening at the distal side beyond the medicine discharge port, for facilitating blood flow from either one of the first opening and the second opening to the other one of the first opening and the second opening.

With the infusion catheter according to the present invention, the stenosed part of the blood vessel can be expanded by positioning and inflating the balloon in the stenosed part in the same manner as the known balloon catheter. During the expansion step, the proximal side of the balloon can communicate with the distal side of the balloon via the blood passage, thereby maintaining the blood flow between the upstream and downstream sides of the stenosed part. Therefore, expansion step can be executed over a long period of time and the infusion catheter can be applied even to the patient sensitive to ischemia.

After the expansion step, the balloon is contracted, the infusion catheter is retreated slightly, the balloon is again inflated and the medicine is discharged from the medicine discharge port. Since the medicine discharge port is provided adjacent the distal end of the balloon, the part of the blood vessel adjacent the distal end of the balloon or the expanded lesion part, is filled with the medicine. Since the second opening of the blood passage for maintaining the blood flow is disposed at the distal side, beyond the medicine discharge part, the medicine is kept between the distal end of the balloon and the second opening in the blood passage. Therefore, while the blood flow is maintained, a rather concentrated medicine can be administered to the lesion part.

Although blood mixes with the medicine adjacent the second opening, it was experimentally confirmed that such mixture proceeds rather slowly and does not inhibit the administration of the concentrated medicine over a long period of time. If the region in which the blood and the medicine are mixed is expanded, just by adding a slight amount of medicine, the region can be moved toward the distal end of the infusion catheter. The medicine can be added as required.

The infusion catheter according to the present invention includes a longitudinal catheter having a proximal end and a distal end. A balloon is provided adjacent the distal end of the catheter shaft, but spaced therefrom. The balloon is inflatable and contractible by supplying and discharging a medium to and from the balloon via a first lumen formed in the catheter shaft. A second lumen is formed in the catheter shaft for introducing medicine infused from the proximal end to a medicine discharge port provided adjacent the distal side of the balloon. A third lumen, or blood passage, is formed in the catheter shaft and provided with a first opening between the balloon and the proximal end of the catheter shaft, and a second opening between the medicine discharge port and the distal end of the catheter shaft. The third lumen, or blood passage, facilitates blood flow from either one of the first opening and the second opening to the other one of the first opening and the second opening.

The first, the second and the third lumens formed in the catheter shaft form the balloon expansion fluid passage, the medicine passage and the blood passage, respectively.

The first lumen communicates with a port connected to a pump or other source of the balloon expansion fluid or medium at the proximal end of the catheter shaft and communicates with the balloon. The balloon expansion fluid can be gas or liquid.

The second lumen communicates with a port connected to an infuser or other source of the medicine at the proximal end of the catheter shaft and communicates with the medicine discharge port. The medicine discharge port is disposed before the second opening of the third lumen, and is formed in the periphery of the catheter shaft slightly distant from the distal end of the infusion catheter.

When the third lumen, or blood passage, is extended from the proximal end to the distal end of the catheter shaft, the third lumen can also form a guide wire passage, in which the second opening corresponds to the distal open end of the catheter shaft, the first opening is disposed at the proximal side of the balloon and a a guide wire port provided at the proximal end of the catheter shaft communicates with the third lumen.

The aforementioned is a so-called over the wire type catheter. By passing the guide wire from the guide wire port to the second opening of the third lumen, a mono-rail type or a rapid exchange type infusion catheter can be provided.

Alternatively, in the catheter shaft, two lumens corresponding to the first and second lumens are formed, while another tube can be disposed parallel the catheter shaft for forming the blood passage. In the alternative structure, when the balloon, the medicine discharge port, the first and second openings in the blood passage are positioned in the same manner as in the first aspect of the present invention, a desired object can be attained. However, the aforementioned infusion catheter is more effective than the alternative structure, in that the combined sectional areas of the lumens are minimized to reduce the diameter of the catheter shaft.

A second aspect of the present invention provides an infusion catheter including an inflatable and contractible balloon, a medicine discharge port provided between the proximal end of the catheter shaft and the balloon for discharging the medicine to the blood vessel, and a blood passage with a first opening located between the proximal end of the catheter shaft and the medicine discharge port and a second opening located at the distal side of the balloon, for flowing blood from either one of the first opening and the second opening to the other one of the first opening and the second opening.

Also with the infusion catheter of the second embodiment, the stenosed part can be expanded by positioning and inflating the balloon in the stenosed part in the same manner as in the known balloon catheter. During the expansion step, the proximal side of the balloon can communicate with the distal side of the balloon via the blood passage, thereby maintaining the blood flow between the upstream and downstream sides of the stenosed part. Therefore, the expansion step can be executed over a long period of time and the infusion catheter can be applied even to the patient sensitive to ischemia.

After the expansion step, the balloon is once contracted, the infusion catheter is advanced slightly, the balloon is again inflated and the medicine is discharged from the medicine discharge port. Since the medicine discharge port is provided adjacent the proximal side of the balloon, the part of the blood vessel adjacent the proximal end of the balloon, i.e. the expanded lesion part, is filled with the medicine. Since the first opening of the blood passage for maintaining the blood flow is located between the proximal end of the catheter shaft and the medicine discharge part, the medicine is kept between the balloon and the first opening of the blood passage. Therefore, while blood flow is maintained, a concentrated medicine can be administered to the lesion part of the blood vessel.

Also in the infusion catheter of the second aspect, the blood and the medicine are mixed in the vicinity of the first opening. Such mixture does not inhibit the administration of the medicine. The medicine can be added to expel the mixture as required.

In the infusion catheter, a longitudinal catheter shaft is extended from a proximal end to a distal end of the infusion catheter and is provided with the balloon adjacent the distal end of the catheter shaft but spaced therefrom. The balloon is inflatable and contractible by the fluid supplied to or discharged from the balloon. A first lumen is formed in the catheter shaft for introducing the fluid supplied from the proximal end into the balloon, a second lumen is formed in the catheter shaft for introducing the medicine infused from the proximal end to the medicine discharge port provided adjacent the proximal end of the balloon, and a third lumen formed in the catheter shaft and provided with the first opening adjacent the distal end of the balloon and the second opening at the proximal side before the medicine discharge port, for facilitating blood flow from either one of the first opening and the second opening to the other one of the first opening and the second opening. The first, second and third lumens formed in the catheter shaft form the balloon expansion fluid passage, the medicine passage and the blood passage, respectively.

The first lumen in the second aspect of the present invention is the same as that in the first aspect of the present invention.

The second lumen of the second aspect is functionally the same as that of the first aspect, however, structurally, the position of the medicine discharge port is different.

The third lumen of the second aspect is functionally the same as that of the first aspect, however, structurally the position of the first and second openings are different. In the same manner as in the first aspect, the third lumen can include a passage for receiving a guide wire, as required.

Alternatively, also in the catheter shaft of the second aspect, two lumens corresponding to the first and second lumens are formed, while another tube can be disposed parallel the catheter shaft for forming the blood passage. In the alternative structure, when the balloon, the medicine discharge port and the first and second openings in the blood passage are positioned in the same manner as the second aspect of the present invention, a desired object can be attained. However, the infusion catheter of the second aspect of the present invention is more effective than the alternative structure, in that the combined sectional areas of the lumens are minimized to reduce the diameter of the catheter shaft.

Since the infusion catheter of the first aspect can be retreated slightly after the expansion step for the administration of the medicine, it is easier to handle as compared with the infusion catheter of the second aspect. In the infusion catheter of the second aspect, however, the medicine discharge port is adjacent the proximal end of the balloon. No medicine passage is required inside the balloon. Therefore, the diameter of the balloon is reduced. The selection of the infusion catheter depends on the diameter of the blood vessel and where the infusion catheter is to be applied.

BRIEF DESCRIPTION OF THE DRAWINGS

The invention will now be described, by way of example, with reference to the drawings, in which.

DETAILED DESCRIPTION OF THE PREFERRED EMBODIMENTS

First Embodiment

Figure 1:
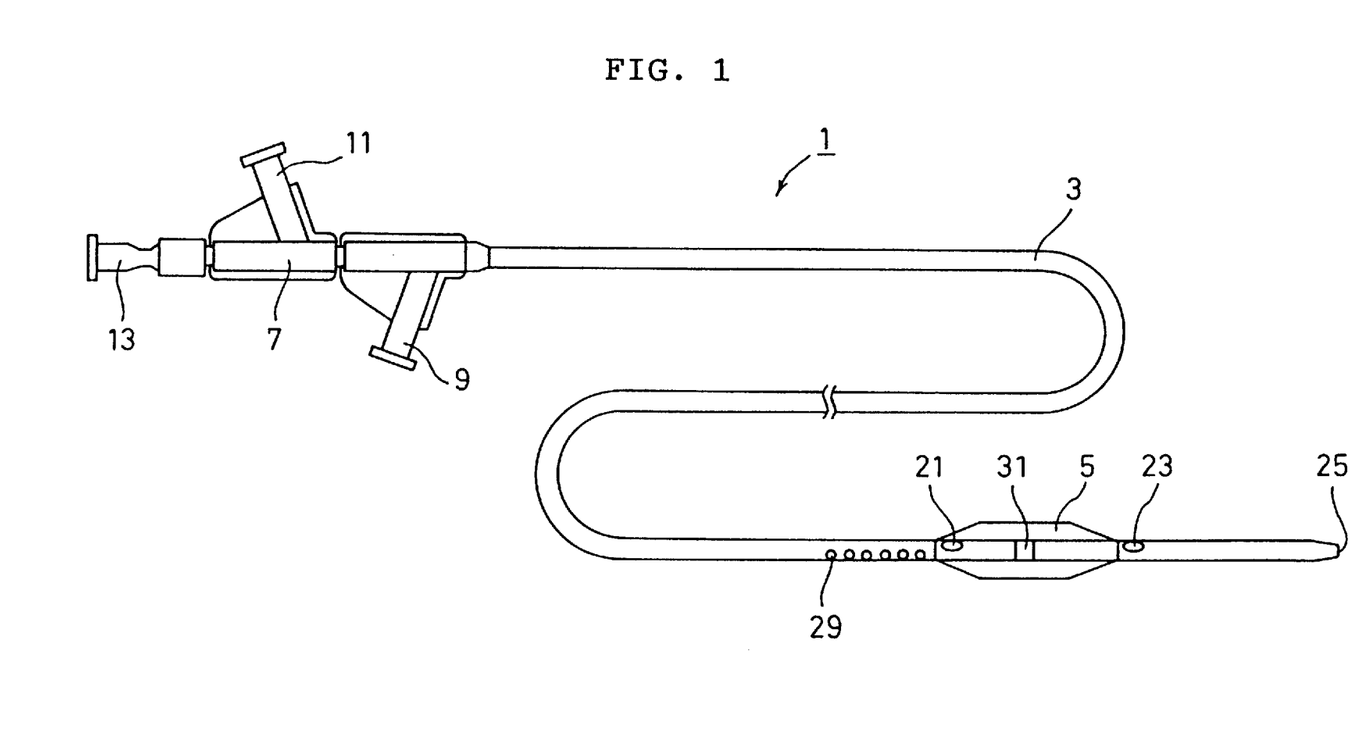
FIG. 1 is a front view of an infusion catheter according to a first embodiment.

In the first embodiment, as shown in FIG. 1, an infusion catheter 1 is composed of a flexible catheter shaft 3 which defines a longitudinal axis, a balloon 5 provided on the outer periphery of the distal end of the catheter shaft 3, and a connector 7 provided at the proximal end of catheter shaft 3. The connector 7 is provided with an expansion liquid supply port 9, a medicine supply port 11 and a guide wire port 13.

Figure 2:
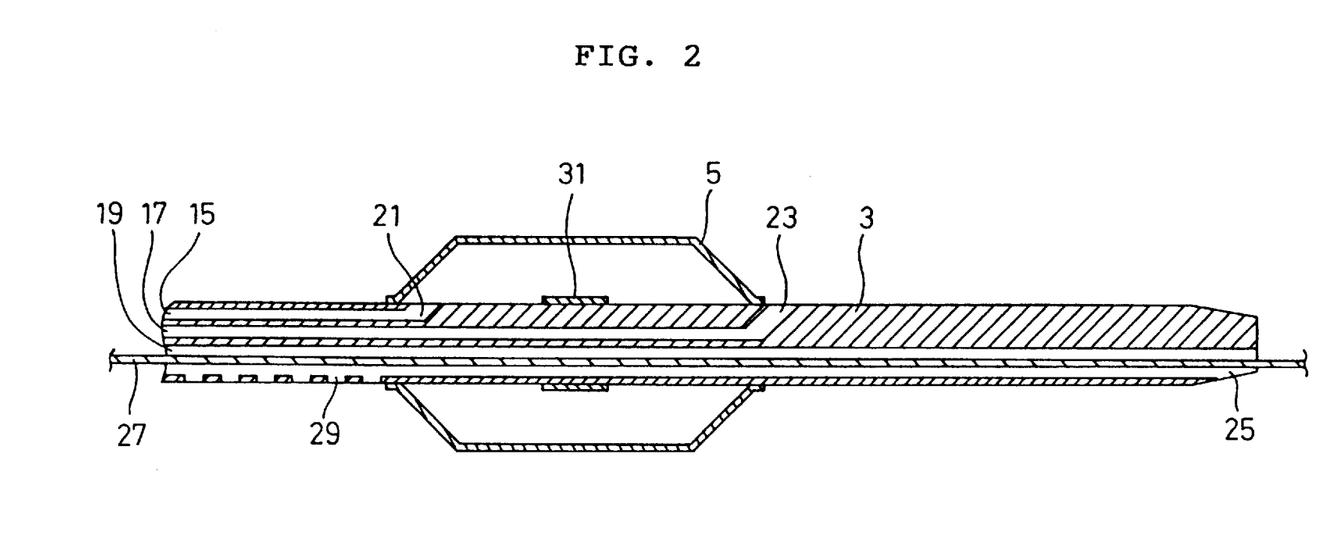
FIG. 2 is a sectional view, with parts broken away, of the first embodiment of the infusion catheter.

Inside the catheter shaft 3, as shown in FIG. 2, first, second and third lumens 15, 17 and 19 are extended parallel to one another. FIG. 2 shows these three lumens in the same cross section. Preferably, however, the lumens 15, 17 and 19 are densely disposed, such that the outer diameter of catheter shaft 3 can be minimized.

The first lumen 15 has one end that communicates with the expansion liquid supply port 9 shown in FIG. 1, and another end that communicates with a balloon port 21 inside the balloon 5. Accordingly, the expansion liquid is introduced from the expansion liquid supply port 9 through the first lumen 15 into the balloon 5.

The second lumen 17 has one end that communicates with the medicine supply port 11 shown in FIG. 1, and another end that communicates with an medicine discharge port or an infusion port 23 provided beyond the balloon 5, adjacent the distal end of the catheter shaft 3. Accordingly, medicine introduced from the medicine supply port 11 is discharged from the infusion port 23.

The third lumen 19 has one end that communicates with the guide wire port 13 shown in FIG. 1, and another end that communicates with an open end 25 provided at a distal tip of the catheter shaft 3. A guide wire 27 is passed through the third lumen 19. A plurality of side holes 29 communicating with the third lumen 19 are formed in the periphery of catheter shaft 3 such that the balloon 5 is interposed between the side holes 29 and the distal tip of the catheter shaft 3. Accordingly, blood flows via the third lumen 19 either way between the side holes 29 and the open end 25.

A metal marker 31 is provided inside the balloon 5 such that the position of balloon 5 is confirmed with X-ray.

Figure 3A:
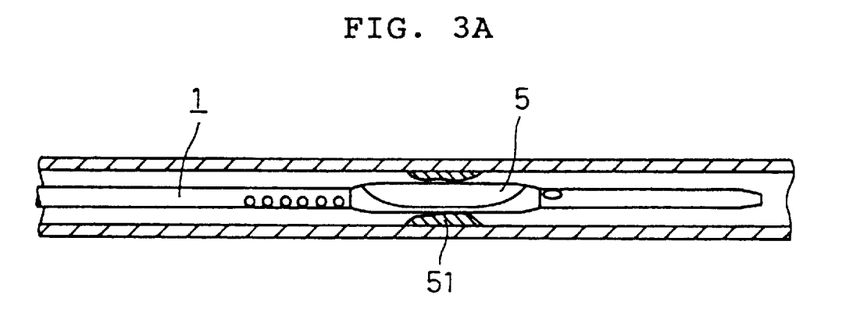
FIGS. 3A, 3B and 3C are diagrammatic views showing the first embodiment of the infusion catheter in use.
Figure 3B:
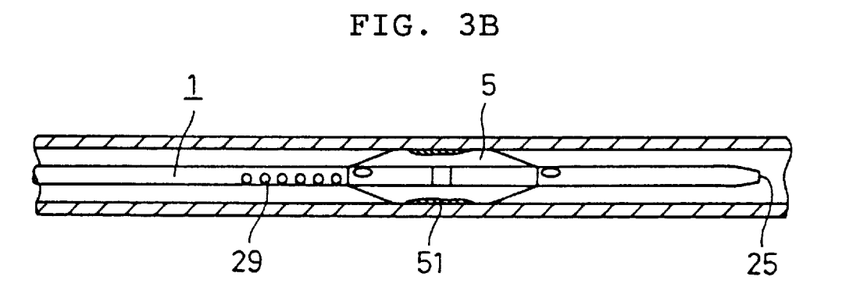
Figure 3C:
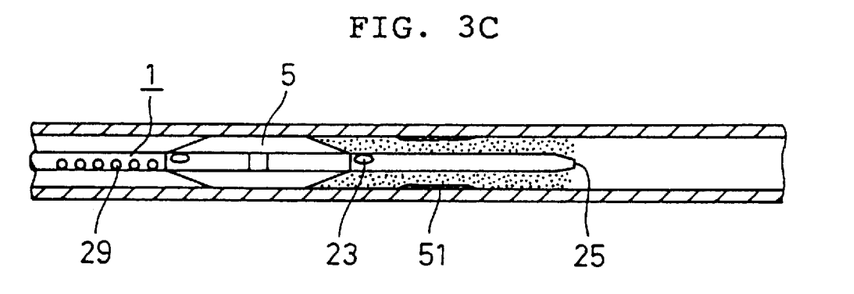

The operation of the infusion catheter 1 is now explained referring to FIGS. 3A, 3B and 3C.

First, the pressure inside the balloon 5 is reduced via the expansion liquid supply port 9, so that the balloon 5 is contracted. A guide catheter having a guide wire 27 (not shown in FIGS. 3A, 3B and 3C) is inserted into a blood vessel, the tip of the guide catheter is guided toward the lesion part 51 of the blood vessel to be expanded, and the infusion catheter 1 with the guide wire 27 passed therethrough is inserted into the blood vessel following the guide catheter. The guide wire 27 is then advanced through the lesion part 51 of the blood vessel so that the infusion catheter 1 can be advanced along the guide wire 27, until the balloon 5 is positioned within the lesion part 51 as shown in FIG. 3A. The position of the balloon 5 is confirmed via an X-ray of the marker 31.

After the balloon 5 is positioned within the lesion part 51 of the blood vessel, the expansion liquid is delivered from the expansion liquid supply port 9 into the balloon 5. As shown in FIG. 3B, the balloon 5 is expanded, thereby causing the lesion part 51 to be expanded. While the balloon 5 is positioned within the lesion part 51 of the blood vessel, blood flow is achieved via the communicating side holes 29, third lumen 19 and open end 25. Depending on the orientation of the infusion catheter 1 within the blood vessel, this configuration maintains blood flow in either of two directions, i.e. from the side holes 29, through the third lumen 19, to the open end 25, or alternatively, from the open end 25, through the third lumen 19, to the side holes 29. Therefore, the lesion part 51 of the blood vessel can be expanded over a long period of time, and the infusion catheter 1 can be applied even to a patient sensitive to ischemia.

Subsequently, the balloon 5 is contracted and the infusion catheter 1 is retreated slightly, for example, by the length of balloon 5. As shown in FIG. 3C, the balloon 5 is again expanded and medicine is delivered from the medicine supply port 11, through the second lumen 17 and discharged from the infusion port 23 to the vicinity of legion part 51. The part of the blood vessel at the distal end of balloon 5 is thus filled with the medicine. The blood flow is maintained by the third lumen 19. Since the open end 25 is positioned at the distal tip and spaced apart from the infusion port 23, the medicine is kept in the blood vessel between the open end 25 and the infusion port 23 as shown by the dots in FIG. 3C. Therefore, while the blood flow is maintained, a relatively high concentrated medicine can be administered to the legion pat 51.

With the infusion catheter 1, only the target lesion part is expanded and a concentrated medicine is administered to the expanded lesion part. Therefore, the inner wall of the blood vessel is prevented from being unnecessarily damaged. Additionally, the laborious work of replacing catheters for the expansion step and the administration step is obviated.

Second Embodiment

The components of the second embodiment identified in the figures with reference characters having the last two digits the same as those in the first embodiment are alike in function with those of the first embodiment, and are not detailed hereinafter.

Figure 4:
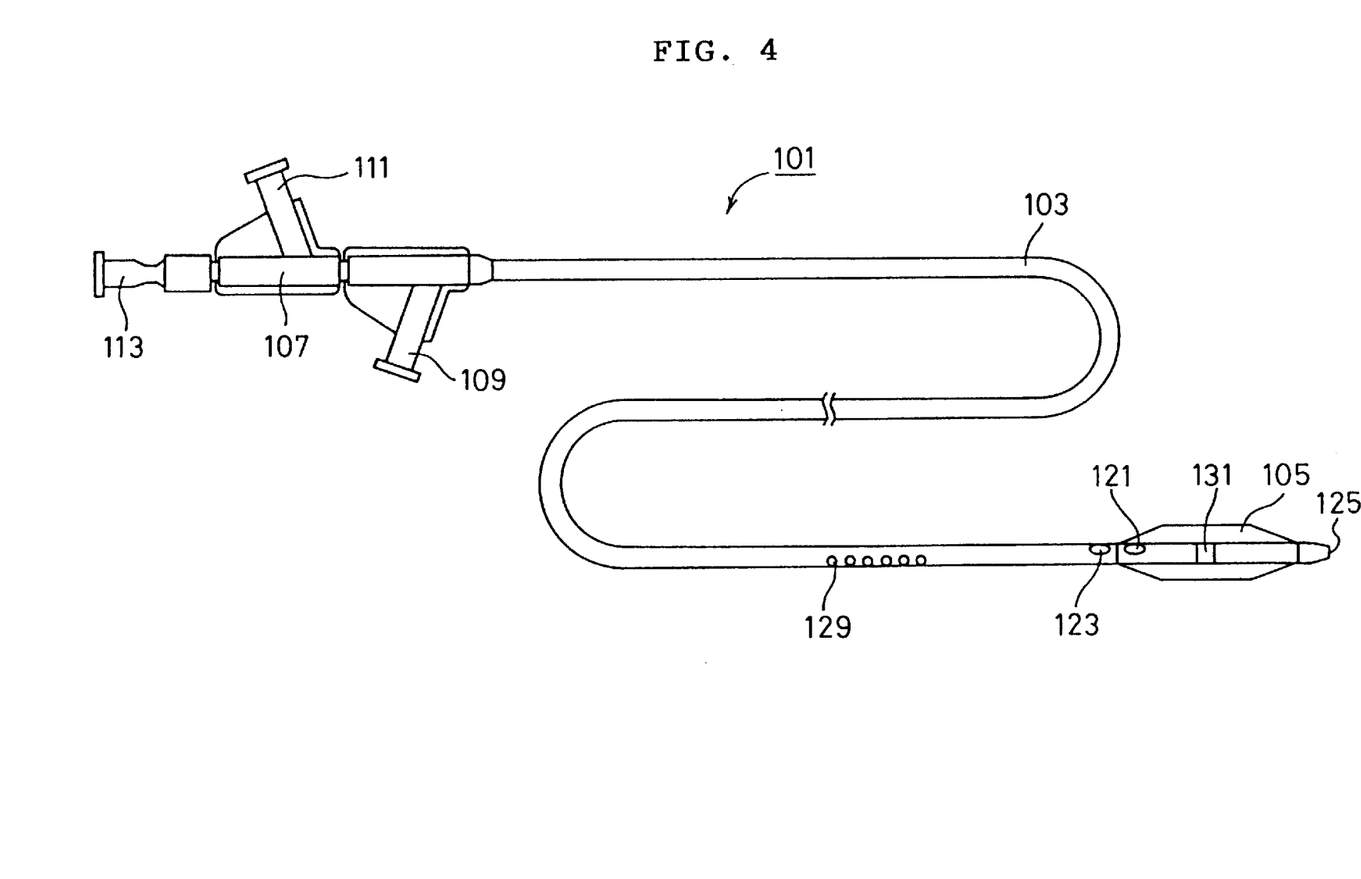
FIG. 4 is a front view of an infusion catheter according to a second embodiment.

In the second embodiment, as shown in FIG. 4, an infusion catheter 101 is composed of a catheter shaft 103, a balloon 105 having a balloon port 121 and a marker 131 inside, and a connector 107. The connector 107 is provided with an expansion liquid supply port 109, a medicine supply port 111 and a guide wire port 113.

Figure 5:
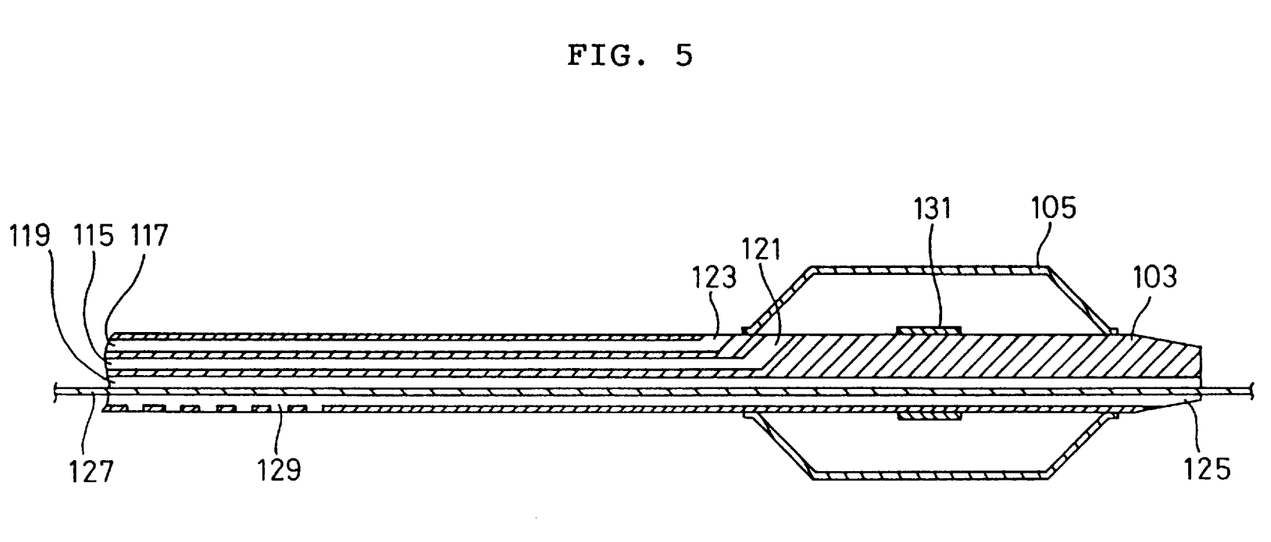
FIG. 5 is a sectional view, with parts broken away, of the second embodiment of the infusion catheter.

Inside the catheter shaft 103, as shown in FIG. 5, first, second and third lumens 115, 117 and 119 are extended parallel to one another, for illustration purposes. In the same manner as the first embodiment, the expansion liquid is introduced from the expansion liquid supply port 109, through the first lumen 115, into the balloon 105. The medicine is introduced from the medicine supply port 111, through the second lumen 117, into an infusion port 123. The third lumen 119 has a guide wire 127 passed therethrough, and forms the blood passage between an open end 125 and side holes 129.

As shown in FIG. 4, the infusion catheter 101 is different from the infusion catheter 1 of the first embodiment, in that the infusion port 123 is positioned adjacent the proximal end of the balloon 105. As shown in FIG. 5, the second lumen 117 is not extended through the balloon 105, the side holes 129 are spaced at a predetermined interval from the infusion port 123 toward the proximal end of the catheter shaft 103, and the open end 125 is provided in the vicinity of the distal end of the balloon 105, irrespective of the position of the infusion port 123.

Figure 6A:
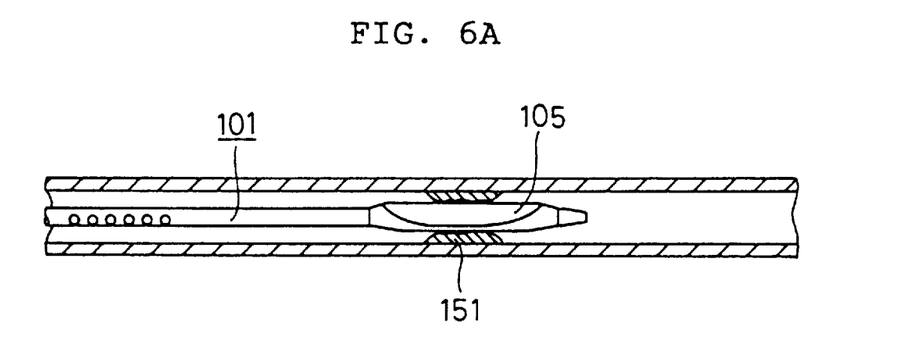
FIGS. 6A, 6B and 6C are diagrammatic views showing the second embodiment of the infusion catheter in use.
Figure 6B:
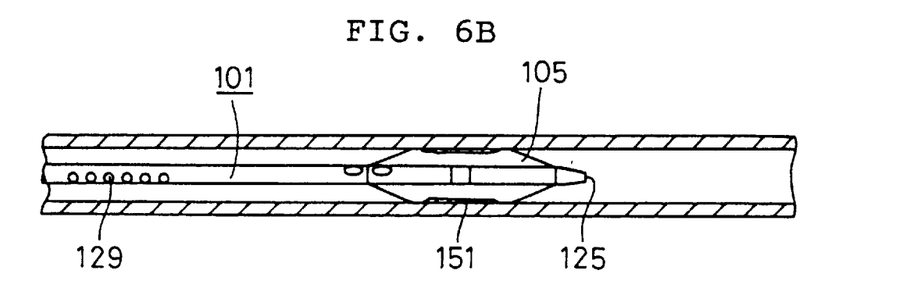
Figure 6C:
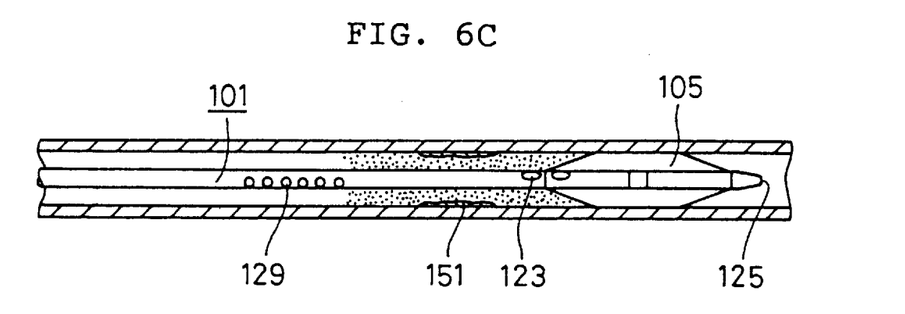

The operation of the infusion catheter 101 is now explained referring to FIGS. 6A, 6B and 6C.

In the same manner as the first embodiment, the infusion catheter 101 is advanced along the guide wire 127 in the blood vessel, until the balloon 105 is positioned within a lesion part 151 as shown in FIG. 6A.

After positioning the balloon 105, the expansion liquid is delivered from the expansion liquid supply port 109, through the first lumen, into the balloon 105. As shown in FIG. 6B, the balloon 105 is inflated, thereby causing the lesion part 151 to be expanded. While the balloon 105 is positioned within the lesion part 151 of the blood vessel, blood flow is achieved via the communicating side holes 129, third lumen 119 and open end 125. Again, depending on the orientation of the infusion catheter 101 within the blood vessel, this configuration maintains blood flow in either of two directions. Therefore, the lesion part 151 of a patient can be expanded over a long period of time, and the infusion catheter 101 can be applied even to a patient sensitive to ischemia.

Subsequently, the balloon 105 is contracted and, different from the first embodiment, the infusion catheter 101 is advanced slightly, for example, by the length of balloon 105. As shown in FIG. 6C, the balloon 105 is again expanded and medicine is delivered from the medicine supply port 111 through the second lumen 117 and discharged from the infusion port 123 to the vicinity of the legion part 151. The part of the blood vessel at the proximal end of the balloon 105 thus receives the medicine. The blood flow is maintained by the third lumen 119. Since the side holes 129 are spaced apart from the infusion port 123 and located toward the proximal end of catheter shaft 103, the medicine is kept in the blood vessel between the side holes 129 and the infusion port 123 as shown by the dots in FIG. 6C. Therefore, while the blood flow is maintained, a relatively high concentrated medicine can be administered to the legion part 151.

Like the first embodiment, with the infusion catheter 101, only the target lesion part is expanded and a concentrated medicine is administered to the expanded lesion part. Therefore, the inner wall of the blood vessel is prevented from being unnecessarily damaged, and the laborious work of replacing catheters for the expansion step and the administration step is obviated.

Unlike the first embodiment, the second lumen 117 is not extended through the balloon 105. Therefore, the balloon 105, when contracted, is smaller in diameter than the balloon 5 of the first embodiment.

In the first embodiment, at the administration step subsequent to the expansion step, the infusion catheter 1 can be pulled back slightly. Therefore, the infusion catheter 1 is easier to handle than the infusion catheter 101 of the second embodiment.

The preferred embodiment of the infusion catheter depends upon the diameter of the blood vessel to which the infusion catheter is to be applied, the skill of a doctor, and the like.

This invention has been described above with reference to the preferred embodiments as shown in the figures. Modifications and alterations may become apparent to one skilled in the art upon reading and understanding the specification. Despite the use of the specific embodiments for illustration purposes, the invention is intended to include all such modifications and alterations within the spirit and scope of the appended claims.

What is claimed is:

1. An infusion catheter for supplying medicine upstream of a lesion formed in a blood vessel following expansion of a balloon, said infusion catheter comprising:

an elongate catheter shaft having a proximal end, a distal end, a first lumen for supplying and removing a fluid medium from a balloon, and a second lumen having a medicine discharge port for supplying medicine to the blood vessel, and both the first and second lumens being supported by the catheter shaft;

a balloon being located adjacent to the distal end of said catheter shaft but spaced therefrom, said balloon communicating with said first lumen and being inflatable and contractible such that said balloon inflates when the fluid medium is supplied to said balloon and contracts when the fluid medium is removed from said balloon;

a blood passage being provided in said catheter shaft for bypassing blood passed both said balloon and said medicine discharge port, said blood passage having a first opening located between the proximal end of said catheter shaft and said balloon and a second opening being located between said balloon and the distal end of said catheter shaft; and the medicine discharge port being located between said balloon and the second opening of said blood passage such that during use, the medicine is introduced into the blood vessel proximate the lesion but spaced from the second opening of said blood passage thereby facilitating the medication to medicate the lesion.

2. An infusion catheter according to claim 1, wherein the first opening of said blood passage comprises a plurality of side holes.

3. An infusion catheter according to claim 1, wherein said catheter shaft has a marker positioned inside said balloon, said marker being x-rayable such that balloon position is confirmable via x-ray.

4. An infusion catheter according to claim 1, wherein the distal end of said catheter shaft terminates at a distal tip, and the second opening of said blood passage is provided in the distal tip.

5. An infusion catheter according to claim 4, wherein said catheter shaft comprises a third lumen communicating with said blood passage, said third lumen having a guide wire port located at the proximal end of said catheter shaft, said third lumen adapted to receive a guide wire such that, when received, said guide wire is extendible through said guide wire port, said third lumen and said blood passage.

6. An infusion catheter for supplying medicine downstream of a lesion formed in a blood vessel, following expansion of a balloon, said infusion catheter comprising:

an elongate catheter shaft having a proximal end, a distal end, a first lumen for supplying and removing a fluid medium from a balloon, and a second lumen having a medicine discharge port for supplying medicine to the blood vessel, and both the first and second lumens being supported by the catheter shaft;

a balloon being located adjacent to the distal end of said catheter shaft but spaced therefrom, said balloon communicating with said first lumen and being inflatable and contractible such that said balloon inflates when the fluid medium is supplied to said balloon and contracts when the fluid medium is removed from said balloon;

a blood passage being provided in said catheter shaft for bypassing blood passed both said medicine discharge port and said balloon, said blood passage having a first opening located between the proximal end of said catheter shaft and said balloon and a second opening being located between said balloon and the distal end of said catheter shaft; and the medicine discharge port being located between the first opening of said blood passage and said balloon such the medicine is introduced, during use, into the blood vessel, via said second lumen, proximate the lesion but spaced from the first opening of said blood passage thereby facilitating the medication to medicate the lesion.

7. An infusion catheter according to claim 6, wherein the first opening of said blood passage comprises a plurality of side holes.

8. An infusion catheter according to claim 6, wherein said catheter shaft has marker positioned inside said balloon, said marker being x-rayable such that balloon position is confirmable via x-ray.

9. An infusion catheter according to claim 6, wherein the distal end of said catheter shaft terminates at a distal tip, and the second opening of said blood passage is provided in the distal tip.

10. An infusion catheter according to claim 9, wherein said catheter shaft comprises a third lumen in communication with said blood passage, said third lumen having a guide wire port located at the proximal end of said catheter shaft, said third lumen adapted to receive a guide wire such that, when received, said guide wire is extendible through said guide wire port, said third lumen and said blood passage.

11. An infusion catheter for supplying medicine to a lesion formed in a blood vessel following expansion of a balloon, said infusion catheter comprising:

an elongate catheter shaft having a proximal end and a distal end;

a blood bypass being provided in said catheter shaft for bypassing blood past a lesion, said blood passage having a first opening being located remote from the distal end of said catheter shaft and a second opening being located adjacent the distal end of said catheter shaft to facilitate the bypass of blood past the lesion during use;

a balloon being located adjacent to, but spaced from the distal end of the catheter shaft, between the first and second openings of the blood bypass, and a first lumen communicating with the balloon for supplying and removing a fluid medium from the balloon;

a medicine discharge port for supplying medicine to the blood vessel, the medicine discharge port being located between the first and second openings of the blood bypass but spaced from the balloon, and a second lumen communicating with the medicine discharge port; and both the first and second lumens being supported by the catheter shaft, whereby when the medicine discharge port is located proximate the lesion and medicine is introduced to the lesion, via the second lumen, the blood bypass facilitates a continued flow of blood through the blood vessel while facilitating prolonged exposure of the medication to the lesion.

12. An infusion catheter according to claim 11 wherein the balloon is located between the first opening of the blood bypass and the medicine discharge port.

13. An infusion catheter according to claim 11 wherein the medicine discharge port is located between the first opening of the blood bypass and the balloon.

* * * * *